United States Patent [19]

McAllister et al.

[11] Patent Number: 5,656,428
[45] Date of Patent: Aug. 12, 1997

[54] HOMOGENEOUS BIOASSAY USING ACOUSTIC EMISSION SPECTROSCOPY

[75] Inventors: Douglas J. McAllister, Cape Elizabeth; Ryszard M. Lec, Orono, both of Me.

[73] Assignee: Biode, Inc., Bangor, Me.

[21] Appl. No.: 303,212

[22] Filed: Sep. 8, 1994

[51] Int. Cl.$^6$ .................... G01N 33/536; G01N 33/558
[52] U.S. Cl. .................... 435/6; 422/127; 435/283.1; 435/286.1; 435/287.1; 435/287.2; 436/514; 436/536; 436/807; 204/193; 204/400; 310/311; 310/348; 73/570; 73/587; 73/590; 73/645; 73/646; 73/649; 73/658; 73/659
[58] Field of Search ....................... 422/127; 435/6, 435/283.1, 286.1, 287.1, 287.2; 436/514, 536, 807; 204/193, 400; 310/311, 348; 73/570, 587, 590, 645, 646, 649, 658, 659

[56] References Cited

PUBLICATIONS

D. Betteridge et al., "Acoustic Emissions From Chemical Reactions", Anal. Chem. vol. 53, pp. 1064–1073, 1981.
Sawada and Abe "Acoustic Emissions Arising From the Glation of Sodium Carbonate & Calcium Chloride" Anal. Chem. vol. 5, pp. 366–367 (1985).
Sawada et al. "Acoutics Emission From Phase Transition of Some Chemicals", Anal. Chem. vol. 57, pp. 1743–1745 (1985).
Wentzel & Wade, "Chemical Acoustic Emission Analysis in Frequency Donrain", Anal. Chem, vol. 61, pp. 2638–2642 (1989).
Wentzel et al. "Evaluation of Acoustic Emission as a Means of Quantitative Chemical Analysis", Anal. Chem Acta, vol. 246, pp. 43–53 (1991).
S.W. Bang, R.M. Lec, J.M. Genco et al., "Acoustic Emission Chemical Sensor:", IEEE 1993 Ultrasonics Symposium (Nov. 2-5, 1993).

Primary Examiner—Christopher L. Chin
Attorney, Agent, or Firm—William B. Ritchie

[57] ABSTRACT

A system and method for homogeneous bioassay uses acoustic energy emissions. A measurement cell is designed for binding reactions of mobile biorecognition molecules. The binding reaction contained in the measurement cell is for example a ligand/receptor binding reaction or a complementary nucleic acid binding reaction. A passive acoustic energy transducer is coupled to the measurement cell for detecting acoustic energy generated by the binding reaction of mobile biorecognition molecules. The passive acoustic energy transducer generates a corresponding analog electrical signal. A signal conditioner coupled to the passive acoustic energy transducer filters and amplifies the electrical signal. A signal analyzer determines spectra of the conditioned electrical signal corresponding to characteristic acoustic energy emissions of the binding reaction of mobile biorecognition molecules. The transducer and signal analyzer may be constructed for spectral analysis of a broad band frequency spectrum in the frequency domain or spectral waveform analysis of a narrow band amplitude spectrum in the time domain. The homogeneous bioassay is applicable for example to ligand/receptor binding reactions such as antigen/antibody binding reactions and enzyme/substrate binding reactions and to complementary nucleic acid binding reactions such as DNA/DNA and RNA/DNA binding reactions.

38 Claims, 8 Drawing Sheets

HOMOGENEOUS BIOASSAY USING ACOUSTIC EMISSION SPECTROSCOPY

TECHNICAL FIELD

This invention relates to a new homogeneous assay for binding reactions of biorecognition molecules. The invention is applicable for example for assaying antigen/antibody binding reactions, enzyme/substrate binding reactions, abzyme/substrate binding reactions, lectin/carbohydrate binding reactions and generally to ligand/receptor reactions. The invention is also applicable to complementary nucleic acid binding reactions such as DNA/DNA, RNA/DNA, RNA/RNA binding reactions, peptide nucleic acid/DNA binding reactions, PCR reactions, and DNA/protein reactions. The new homogeneous bioassay uses acoustic energy emissions generated by the binding reaction, passively detects the acoustic energy emissions, and analyzes the frequency spectra and the amplitude time domain waveform of acoustic energy emissions characteristic of the particular binding reaction. The invention can be used for identifying and quantifying particular binding reactions of biorecognition molecules.

BACKGROUND ART

Passive acoustic sensors have been used to analyze characteristic acoustic energy emissions generated by inorganic chemical reactions and chemical changes. Some of these chemical changes which produce acoustic energy include liquid-solid and solid-liquid transitions, dissolution, hydration and gelation. Chemical changes are normally accompanied by energy transfer and some of the energy released may be in the form of acoustic waves. Betteridge et al. examined acoustic energy spectra from 43 different chemical systems. They found a correlation between chemical and acoustic events, although some acoustic responses were difficult to explain. They speculated that the thermal changes occurring during chemical reactions were sources of acoustics signals. D. Betteridge et al., "Acoustic Emissions From Chemical Reactions", Anal. Chem. Vol 53, p. 1064–1073 (1981). Sawada and Abe investigated acoustic emissions arising from a gelation of sodium carbonate and calcium chloride. They obtained several acoustic signals during the gelation reaction. They explained the initial acoustic energy signals as thermally caused via exothermic reaction in the gel formation, but interpretation of the other responses needed further experimental work. Sawada and Abe, "Acoustic Emissions Arising From the Gelation of Sodium Carbonate and Calcium Chloride", Anal. Chem. Vol 5, pp 366–367 (1985). Acoustic emission from phase transitions of four chemical systems was investigated by Sawada et al. They found that acoustic energy signals were influenced by changes of volume, heat balance, and reaction rate. Sawada et al., "Acoustic Emission From Phase Transition of Some Chemicals", Anal. Chem. Vol 57, pp 1743–1745 (1985).

A model process, the hydration of silica gel, was investigated in detail by Belchamber et al. using acoustic energy emissions. They found that the hydration process for the silica was a two-step process and obtained important information about the kinetics of that process. Their results suggest that acoustic energy monitoring could be an effective way of gaining often unique information about difficult-to-study chemical processes and could be applied for monitoring chemical processes. Belchamber et al., Anal. Chem. Vol 58, p. 1877 (1986).

Wentzel and Wade showed that chemical reactions have their own unique acoustic energy signatures. They analyzed frequency spectra of the acoustic energy signal for several chemical systems using Fourier transform technique. They also found that the different physical processes yield different contributions to acoustic energy response, ie. gas release is shown to result in low-frequency signals, while crystal fracture produces higher frequency range acoustic energy. Wentzel and Wade, "Chemical Acoustic Emission Analysis in Frequency Domain", Anal. chem. vol 61, pp 2638–2642 (1989). Wentzel et al. found that different bubble evolution sites on an enzyme catalytic surface produced repeatable emission wave fronts, and each had its own particular acoustic signature. Wentzel et al. used the enzyme catalase immobilized on the transducer surface to accelerate the conversion of hydrogen peroxide to gas. Wentzel et al. "Evaluation of Acoustic Emission as a Means of Quantitative Chemical Analysis", Anal. chem. Acta, vol 246, pp 43–53 (1991).

Recently, Lec et al. investigated the kinetics of the causticization process using the acoustic energy technique. The causticization process consists of two reactions, a lime slaking reaction and a causticization reaction. It was found that the acoustic energy frequency spectra of these reactions were different. Also, a new mechanism, caused by the ion—ion exchange reaction during the causticization process, has been identified via specific acoustic energy signals. Lec et al., Proc. SPIE Smart Sensing, Processing, & Instrumentation, vol 1918, pp 440–448 (1993) and S. W. Bang, R. M. Lec, J. M. Genco et al., "Acoustic Emission Chemical Sensor", IEEE 1993 Ultrasonics symposium, (Nov. 2–5, 1993).

Generally, acoustic sensors can be categorized as either active or passive. Active sensors transmit an acoustic wave into a medium under test, the acoustic wave interacts with the medium, and measured parameters of the acoustic wave are correlated with medium properties. Passive acoustic sensors measure acoustic signals which are generated in the medium itself during physical or chemical processes.

Research on active acoustic sensors in the biochemical and biomedical areas has occurred for several decades. Active acoustic sensors have been used to detect organic gases, viscosity or ion concentration in solutions. In recent years active acoustic sensors have been used for monitoring immunological reactions. To date, only three types of acoustic devices, a quartz crystal resonator (QCR), the acoustic plate mode (APM) device and the bulk wave (SSBW) device have been used for immunoassay purposes. The methods all involved the surface immobilization of one of the biocomponents, usually the antibody, and use of active acoustic probes.

While active acoustic sensor technology has now been used in biochemical and biological reactions, it has not been conceived to use passive acoustic sensor technology to detect the subtleties of biological reactions such as the binding reactions of biorecognition molecules. It is established that the making and breaking of chemical bonds during chemical reactions generates sufficient acoustic energy emission for distinguishing the chemical changes by the characteristic frequency spectrum of the acoustic emissions over time. It is not obvious or suggested however, that the binding reactions of biorecognition molecules such as antigen/antibody reactions and complementary nucleic acid reactions cause sufficient acoustic emissions and in distinguishing characteristic patterns for discriminating between such similar binding reactions.

Immunoassays are well-known for their selectivity and speed because of the inherent specificity and high binding constants of antibodies. The most desirable immunoassay is one which is homogeneous. In such an assay, the patient specimen containing an unknown level of analyte is mixed directly with the antibody reagent. After some incubation period, a direct result is obtained in the form of a visual observation or instrument measurement of fluorescence, color, chemiluminescence etc. Commercial homogeneous immunoassays can thus be used or added to existing clinical analyzers and are much in demand due to the ease of use. Examples of such assay technologies include Syva's EMIT (TM) assays that are enzyme mediated and Abbott's TDX (TM) that are fluorescence polarization based. These systems are designed to quantitate analytes such as drugs and small molecular weight hormones.

However, with the exception of nephelometry, there are no other homogeneous immunoassay systems which are capable of quantitating detected macromolecules such as proteins. Those immunoassays which do, are heterogenous, requiring multiple separation and wash steps, followed ultimately by a "reporter" system such as an isotope (RIA) or enzyme (ELISA). These later assays, though sensitive, require a minimum assay time of at least 2–3 hours and are discrete, i.e. with single, end-point determination.

Immunonephelometry is used commercially to quantitate clinically significant human proteins and exhibits the inherent simplicity and ease of use of a true homogeneous assay. Specific antiserum is mixed with a dilution of patient serum and the resulting turbidity which develops over time is measured optically by absorbance (turbidimetry) or reflective fluorescence (nephelometry). However, this technology has several major drawbacks. First, the specimen to be tested must have optical clarity i.e. not be turbid or contain solids. Second, the reaction cell or cuvette requires a high quality optical window and usually two. Third, the lower limit of sensitivity is $^{18}10$ µg/ml of antigen protein.

These drawbacks have meant that this technique has been limited in its application to the measurement of selected serum/plasma proteins found in the higher concentrations as specified above. Thus there are a number of clinically significant protein analytes such as tumor markers, ferritin, and β2-microglobulin which are present at lower concentrations and therefore must be assayed by other more tedious and time consuming techniques such as the enzyme linked immunosorbent assay i.e. ELISA. Because of the requirement for specimen clarity, immunoturbidimetry cannot be applied to industrial use. Thus application areas such as food processing are not possible with current homogeneous assays.

OBJECTS OF THE INVENTION

It is therefore an object of the present invention to provide a new homogeneous bioassay using the acoustic energy emissions generated by particular binding reactions of biorecognition molecules. According to the invention the characteristic frequency spectra or characteristic time domain amplitude waveforms sensed from a particular binding reaction of mobile biorecognition molecules can be used to identify the reaction. No separation or washing steps are required.

Another object of the invention is to provide a method for identifying specific binding reactions of multiple mobile biorecognition molecules by constructing and devising acoustic energy emission receivers tuned to particular binding reactions. According to the method the characteristic acoustic emission frequency spectra are first determined in the frequency domain and then amplitude waveforms or amplitude spectra are determined at the active frequencies in the time domain. The frequency and amplitude waveform spectra can provide both qualitative and quantitative analysis.

A further object of the invention is to provide new measurement cells and reaction chambers for binding reactions of biorecognition molecules which minimize interference and optimize collection of acoustic energy emissions at the respective passive acoustic energy transducers. The invention is applicable to both batch monitoring and continuous monitoring.

DISCLOSURE OF THE INVENTION

In order to accomplish these results the invention provides a system for homogeneous bioassay using acoustic energy. A measurement cell is designed for a binding reaction of mobile biorecognition molecules. The binding reaction contained in the measurement cell is selected from the group consisting of ligand/receptor binding reactions and complementary nucleic acid binding reactions. A passive acoustic energy transducer is coupled to the measurement cell for detecting acoustic energy emissions generated by a binding reaction of mobile biorecognition molecules.

The passive acoustic energy transducer generates an analog electric signal corresponding to the acoustic energy detected by the transducer. A signal conditioner is coupled to the passive acoustic energy transducer for filtering and amplifying the electrical signal. A signal analyzer or modulation analyzer is coupled to the signal conditioner for determining spectra of the conditioned electrical signal.

The signal analyzer can be a frequency spectrum analyzer. In that case the system determines the frequency spectra in the frequency domain characteristic of the acoustic emissions of the particular binding reaction. Frequency spectra at successive time intervals can be determined. Or, the signal analyzer can be a time domain analyzer or correlator. In that case the system determines the amplitude spectra in the time domain of selected frequencies characteristic of the acoustic energy emission of a particular binding reaction. Or, the signal analyzer/modulation analyzer can look at both the frequency domain and the time domain.

The frequency spectrum in the frequency domain corresponds to a characteristic acoustic frequency spectrum indicative of the binding reaction of mobile biorecognition molecules. Such a frequency spectrum may serve as a fingerprint or acoustic signature of the particular binding reaction. Alternatively, the time domain analyzer and correlator determines the time domain waveform also referred to herein as the amplitude spectrum through time, of a selected narrow frequency band of the electrical signal corresponding to a narrow frequency band of the acoustic energy emissions. The amplitude spectra or amplitude waveforms in the time domain may also serve as an identification pattern for the particular binding reaction.

A feature of the invention is that the signal analyzer can look at the characteristic frequency spectrum in the frequency domain at selected time intervals for generating a characteristic acoustic emission signature in the frequency domain and for identifying the energetic frequencies of a particular reaction. At each sampling the spectrum analyzer analyzes the frequency spectrum across a frequency domain of selected bandwidth.

The receiver electronics can then be fine tuned to look at selected active or noisy frequencies only, analyzing the amplitude spectrum or waveform in the time domain. Time domain analysis by the signal analyzer provides the basis for both qualitative and quantitive analysis of the binding reaction without the requirement of heterogeneous multiple separation and wash steps. The bioassay of biological binding reactions according to the present invention can therefore be characterized as homogeneous.

The homogeneous bioassay according to the invention is applicable to a variety of ligand/receptor binding reactions selected from the group consisting of antigen/antibody binding reactions, enzyme/substrate binding reactions, abzyme/substrate binding reactions, and lectin/carbohydrate binding reactions. The homogeneous bioassay is also applicable to a variety of complementary nucleic acid binding reactions selected from the group consisting of DNA/DNA reactions, RNA/DNA reactions, RNA/RNA reactions, peptide nucleic acid/DNA reactions, PCR reactions, and DNA/protein reactions.

As used in the specification and claims biorecognition molecules are intended to include such ligand/receptor molecule binding reactions and complementary nucleic acid molecule binding reactions as set forth in the preceding paragraph. Thus biorecognition molecules refer to the highly specific and highly energetic binding reactions characteristic of specifically bonding biological molecules.

The acoustic energy transducer can be a wideband frequency response transducer responsive to a specified broad frequency spectrum of acoustic energy. For this purpose the transducer can be constructed for peak resonance at an odd multiple of one half the wavelength of the center frequency of the specified broad frequency spectrum. For broad band response the transducer can also be provided on an elastic base. A broad specified frequency spectrum e.g. in the KHz, MHz, GHz ranges etc. can be provided. The range can also be extended to the limits of ultrasonic technology. By this arrangement, the actively and energetically emitted frequencies of acoustic energy generated by a particular binding reaction can be identified in the frequency domain and at selected sampling intervals through time. A more sensitive receiver can then be constructed with multiple transducer plates or a multichannel receiver at the sensitive energetic frequencies for identifying a particular binding reaction of biorecognition molecules by amplitude analysis of the selected frequencies in the time domain.

The acoustic energy transducer can also be a narrow band frequency response transducer responsive to a specified narrow frequency spectrum of acoustic energy. Typically such a narrow acoustic energy transducer is designed with a peak resonant frequency at the center frequency of the narrow band. The center frequency is selected to coincide with an active or noisy frequency of the particular binding reaction. The transducer signal output after conditioning is then coupled to a time domain analyzer and correlator for determining and analyzing the amplitude of the selected narrow frequency band of energy in the time domain. Thus, the amplitude spectrum or waveform is determined over selected time intervals. An advantage of the time domain analysis of amplitude at selected frequencies is that the time domain amplitude spectrum can be used to assist quantitating the binding reaction of biorecognition molecules as well as for identifying the occurrence of a particular binding reaction.

The signal conditioner can be set to select a narrow frequency band or channel. The selected frequency is analyzed for its amplitude waveform in the time domain, that is during selected time intervals. A highly specific and finely tuned acoustic "signature" can then be identified in the time domain for each type of binding reaction.

According to another example the acoustic energy transducer can be a multichannel transducer provided by a plurality of transducer plates responsive to different frequency bands or channels of acoustic energy for differentiating by channel the characteristic acoustic energy generated by a particular binding reaction. The transducer plates can each comprise a narrow or wide band frequency response transducer responsive to a different narrow or wide frequency spectrum of acoustic energy. In that case each narrow or wide band frequency response transducer can be constructed for peak resonance at an odd multiple of ½ the wavelength of the center frequency of each specified frequency band. An acoustic energy receiver can therefore be designed and constructed for "tuned" sensitivity to the active frequencies of particular binding reactions and for use in sensing those reactions.

According to an alternative embodiment the function of channelizing the acoustical energy emissions of a particular binding reaction can be accomplished using a channelized receiver coupled to the conditioned signal output of a single acoustic energy transducer. The channelized receiver selects the signal energy in a plurality of channels each covering a small fraction of a broader frequency band. The amplitude spectrum of the signal in each channel or narrow band can then be used to identify a particular binding reaction using for example a pattern recognition system. In addition to identifying an acoustic signature of a known reaction using the channelized amplitude spectra in the time domain, the rate and amplitude of the reaction can also be used to assist in quantifying the reactants.

As used in the specification and claims, reference to an acoustic energy transducer therefore includes broadband acoustic energy transducers, narrow band acoustic energy transducers, and multiband or multichannel acoustic transducers. Multiband and multichannel acoustic transducers can be provided in a number of configurations including separate transducers abutting the reaction chamber of a measurement cell or a stacked array of transducer plates for selecting and responding to acoustic energy emissions at selected frequencies, bands or channels. The acoustic energy transducers may also be in a variety of configurations such as flat or curved shapes. Such acoustic energy transducers may include piezoelectric transducers, magnetostrictive transducers, thermal or pyroelectric transducers, fiber optic sound wave sensors, capacitive electrodynamic transducers, optical interferometer or optical deflection acoustic vibration transducers and generally any appropriate transducer which converts mechanical, acoustical or sound energy to an electrical signal.

In order to increase the efficiency of detection of acoustic energy emissions by the acoustic energy transducers, the transducers may contact or abut the measurement cell through acoustic impedance matching layers performing the function of acoustic quarter wave length transformers and acoustic matching networks. The acoustic impedance matching layers have material characteristics of density and stiffness intermediate between the solid piezoelectric transducer plates or other acoustic energy transducer plates and the aqueous solution of the binding reactants in the reaction chamber. To facilitate transmission of the acoustic energy emissions from the liquid solution into the solid plate transducer, the acoustical impedance matching layers may be an odd multiple of a quarter wave length of the center frequency of a particular frequency band or channel of interest.

According to a preferred example the measurement cell includes a reaction chamber having the passive acoustic energy transducer coupled to one side of the reaction chamber. An acoustic reflecting lens is formed on the opposite side of the reaction chamber for reflecting and focusing acoustic energy generated by a binding reaction of mobile biorecognition molecules onto the transducer. For this purpose, the cover or roof of the reaction chamber may be in the configuration of a parabolic or circular reflector. By way of example, the reaction chamber can be constructed primarily from a solid material such as metal, brass, stainless steel, glass, or plastic.

According to another example the measurement cell includes a binding reaction chamber of multisided polygon cross section. Multiple passive acoustic energy transducers are provided to apply to the sides of the polygon. Each transducer plate faces a respective side of the reaction chamber and is acoustically coupled to the respective side of the reaction chamber by an acoustically transmissive medium. Each transducer plate is responsive to a different frequency band of acoustic energy generated by a binding reaction of mobile biorecognition molecules.

The plurality of transducer plates may similarly be constructed as narrow band frequency response transducers responsive to a different narrow frequency spectrum or band of acoustic energy. Each narrow band frequency response transducer may similarly be constructed for peak resonance at an odd multiple of ½ the wavelength of the center frequency of the specified narrow band spectrum. The signal conditioner is also used for selecting a single frequency band or channel for analysis of amplitude spectra in the time domain. In a preferred example the measurement cell is a three sided reaction chamber of triangular cross section with a plurality of three passive acoustic energy transducers. Other polygon cross sections can of course be used such as square, pentagon, hexagon, etc. The transducers may be curved to enhance reception of acoustic energy.

According to the invention the measurement cell reaction chamber preferably has a very small volume, for example in the range of 0.1 ml to 1.0 ml. The small volume approximates a point source, minimizes interference effects of the acoustic energy emissions from the binding reaction, and facilitates a more coherent wavefront incident on the transducer. The measurement cell may also be designed as a flow through reaction chamber having an inlet end and an outlet end for flow through of a binding reaction mixture at a specified flow rate for continuous monitoring. The inlet end includes multiple inlets for the respective reactants so that the binding reaction does not occur until the reactant molecules are in the reaction chamber. Generally the measurement cell may also be constructed with a narrow band, wideband, or multiband frequency response acoustic energy transducer responsive to narrow band wideband, or multichannel frequency spectra.

The homogeneous bioassay according to the invention provides not only qualitative identification of particular binding reactions, but also the basis for quantitative analysis of reactants. Quantitative analysis is based upon rate of reaction determined by the rate of change of the frequency spectra as well as the amplitude waveform of the signals and can be determined for each particular binding reaction.

The invention also provides a new method for homogeneous bioassay using the new system as hereafter described. According to the broader method of the present invention the system for homogeneous bioassay is first used with a passive acoustic energy transducer responsive over a broad frequency spectrum for determining the characteristic frequency spectra in the frequency domain at successive time intervals. In this way, the active or energetic acoustic energy frequencies of a particular binding reaction can be determined.

A set of passive acoustic energy transducer plates each responsive to a narrow frequency band can then be constructed at the active energetic frequencies of a particular reaction. Alternatively, a channelized receiver can be used selecting multiple channels at the active or noisy frequency bands.

The measurement cell and receiver electronics are thereby "tuned" to a particular reaction and the sensitivity is increased by analyzing the amplitude spectra of the active frequencies in the time domain. A particular reaction might then be identified by its characteristic spectra in both the frequency domain and the time domain. Other objects, features and advantages of the invention are apparent in the following specification and accompanying drawings.

DESCRIPTION OF PREFERRED EXAMPLE EMBODIMENTS AND BEST MODE OF THE INVENTION

Figure 1:
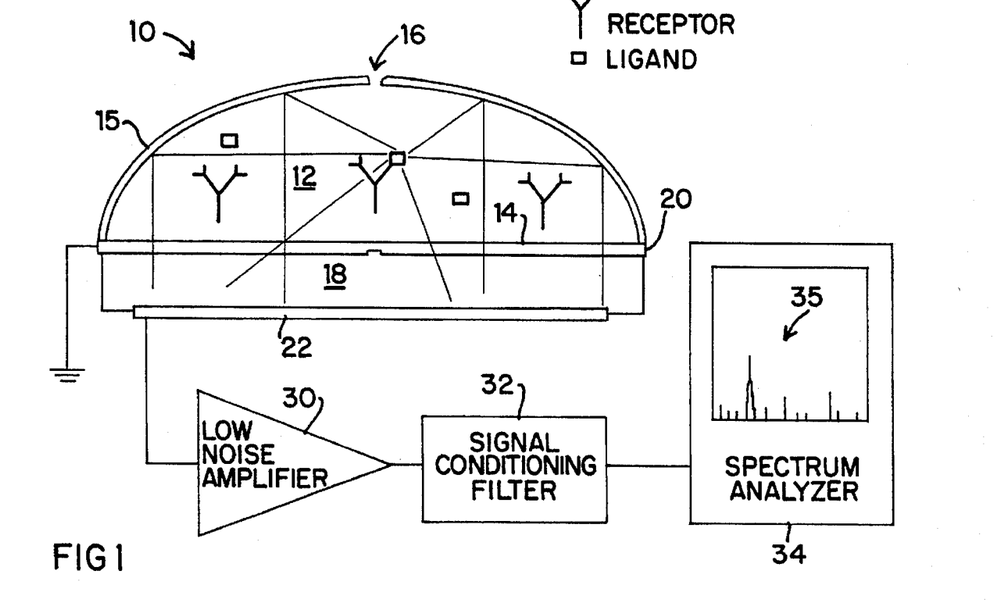
FIG. 1 is a simplified system block diagram of a measurement cell and associated electronics for homogeneous bioassay using the frequency spectra characteristic of acoustic energy emissions in the frequency domain.

A reaction chamber measurement cell 10 and associated electronics for performing a homogeneous bioassay according to the invention are illustrated in FIG. 1. The reaction chamber 12 in which the biorecognition binding reaction occurs is defined by a flat base 14 of material designed to pass acoustical energy into a piezoelectric plate transducer 18 as hereafter described and a curved roof or dome 15 designed to reflect acoustical energy back to the piezoelectric plate transducer 18. The curve of the roof or cover 15 may be in the configuration of a section of a parabola or section of a circle. For example the roof or cover 15 may be a section of a parabolic cylinder or a dome in the configuration of a section of a parabola of rotation. Reactants are admitted through an opening 16 and in this example are shown as generalized receptor molecules such as antibody molecules and generalized ligands such as protein antigens.

The base 14 of the measurement cell 10 overlies an acoustical sensor, for example, a piezoelectric (PZE) plate such as a piezoelectric plate transducer 18 composed, for example, of the ceramic PZT-5A. Conductive electrodes 20 and 22 are applied on either side of the piezoelectric sensor plate 18. The electrodes may be, for example, metal layers vacuum deposited or sputtered onto the PZE plate 18, metal foil, or other metal layers. A typical metal for the electrodes is gold. Electrode 20 is grounded while the electrical signal corresponding to the acoustic emission is derived from electrode 22 as hereafter described.

The acoustical sensor or acoustical transducer 18 may be selected to provide a broad band frequency signal responsive to a broad frequency band of acoustical energy, a narrow band frequency signal responsive only to a narrow frequency band of acoustical energy, or a multiband signal responsive to multiple different spaced apart narrow frequency bands of acoustical energy. Such alternatives are hereafter described.

In the example of FIG. 1 a broad band acoustical transducer is selected in the form of a piezoelectric plate responsive to a broad band of acoustical frequencies with the peak resonance of the transducer plate selected to be at an odd multiple of the half wave length ($n\lambda/2$ where n is an odd integer) of the center frequency of the broad band spectrum. For example the broad band spectrum may be selected anywhere in the kilohertz KHz to the megahertz MHz to the gigahertz GHz range. The broad bandwidth of the selected PZE plate can be enhanced by an elastic material base.

Figure 1A:
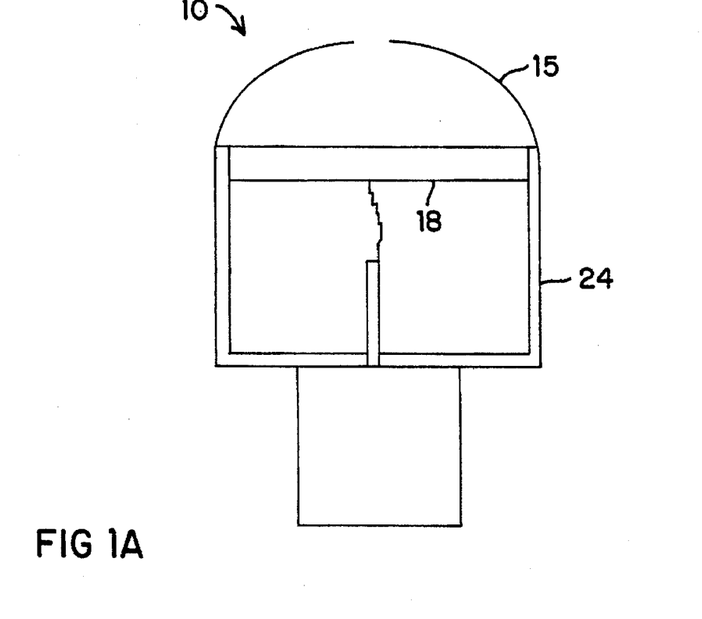
FIG. 1A is a simplified diagram showing a solid material holder for isolating the measurement cell.

By way of example, the parabolic reflector 15 can be made of solid material such as glass, ceramic, plastic, metal such as brass, etc. providing a reflective surface for internally generated acoustic emissions. The cover 15 can be mounted on a similar solid material holder 24 providing isolation of the measurement cell 10 from environmental noise all as shown in FIG. 1A. Returning to FIG. 1, the base 14 may incorporate impedance matching layers for passing acoustical energy generated in the reaction chamber in a water environment to the solid piezoelectric plate. Such impedance matching layers are composed of materials having density and stiffness intermediate between the water and the PZE plate. Matching layers may be composed for example of polypropylene, polystyrene, polycarbonates, acrylic plastic, etc. The impedance matching layers can be formed in the thickness of an odd multiple of the wavelengths of particular interest ($n\lambda/4$ where n is odd), providing the effect of ¼ wavelength transformers.

Each biorecognition event in the reaction chamber 12 of measurement cell 10 results in a burst of acoustic signal energy. Such a biorecognition event may be for example the binding reaction of a known receptor with an unknown ligand or an unknown receptor with a known ligand. For example, the binding reaction of a known/unknown antibody with an unknown/known antigen protein may be used in an immunochemical test. The binding reaction of such an antibody with its specific antigenic protein causes acoustic emission of acoustic energy in many directions. The design of the measurement cell serves to redirect most of the acoustical energy back to the PZE plate acoustic sensor 18. The impedance matching layers 14 ease the acoustic energy into the PZE plate.

The piezoelectric plate 18 in response to the mechanical acoustic energy generates an analog electrical signal at electrode 22 which is amplified by low noise amplifier 30 to a usable signal amplitude for further processing. The analog electrical signal is filtered by signal conditioning filter 32 to eliminate excess environmental noise. Finally, a spectrum analyzer 34 performs a Fourier transformation on the amplified and conditioned analog electrical signal to display the frequency spectrum of the signal.

In the example hereafter described the acoustic signals associated with different biorecognition events in the form of binding reactions of biological molecules have characteristic frequency spectra that may serve as a distinguishing signature or fingerprint of the particular binding reaction. Observation of the acoustic emission signature indicates that the respective biorecognition event is occurring. In the example of FIG. 1 the spectrum analyzer looks at the frequency spectrum in the frequency domain. A subsequent look at selected active frequencies in the time domain can be used for further identification and may also be used to provide an indication of quantity. The frequency spectrum across the broad frequency band determined in the example of FIG. 1 can be used to identify the particularly active or noisy frequencies associated with a particular reaction. As described subsequently analysis can then be made of selected frequencies in the time domain.

It should also be noted that the entire frequency spectrum across a broad frequency band can also be monitored in the time domain by sampling the entire frequency spectrum at successive intervals of time. The changing amplitudes of the respective frequency components of a broad band frequency spectrums are then monitored through time, i.e. in the time domain. The changing or characteristic amplitudes of the broad band spectrum through time can also assist in identifying a particular reaction.

Figure 2:
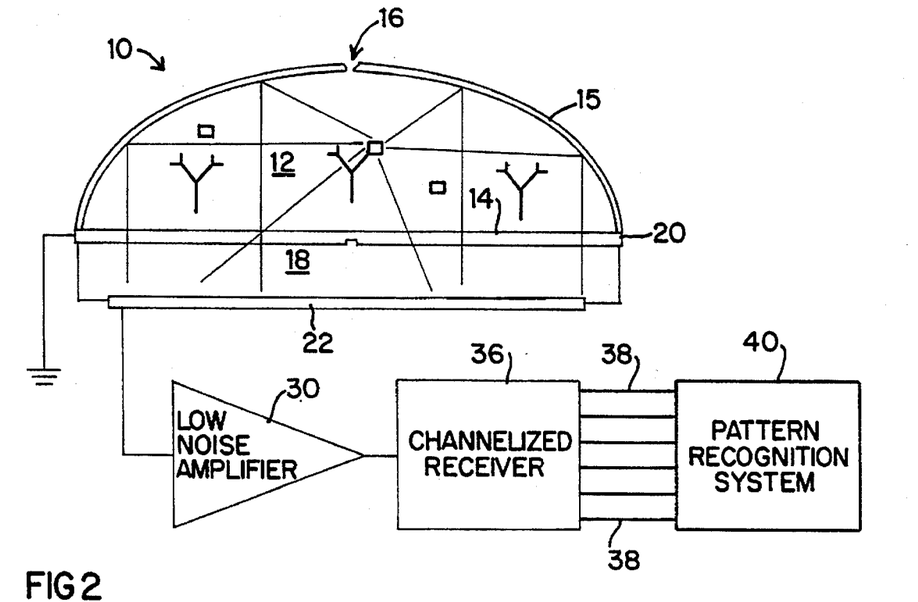
FIG. 2 is a simplified system block diagram of a measurement cell and associated electronics for homogeneous bioassay using amplitude spectra characteristic of acoustic energy emissions in the time domain.

Another analytic approach to identifying a particular binding reaction between a receptor and a ligand or between complementary nucleic acids is illustrated in FIG. 2. Elements of the homogeneous bioassay system of FIG. 2 similar to FIG. 1 are indicated by the same reference numerals. In this case, the selected active or noisy acoustic frequencies or frequency bands of a particular binding reaction have previously been identified for example according to the system and procedure of FIG. 1. In the example of FIG. 2 the amplified usable analog electrical signal from low noise amplifier 30 is input to a channelized receiver 36 constructed to select in this example six narrow frequency bands through appropriate pass band filters. The six narrow frequency bands selected by the multiband channelized receiver 36 are the particularly noisy or active frequencies or frequency bands of the particular binding reaction. The amplitude distribution or history of the selected frequencies in the time domain are input over the six lines 38 into a pattern recognition system 40. The pattern recognition system looks at the amplitude sequence of the selected frequencies in the time domain and compares these with known patterns of the selected binding reaction. Such pattern recognition can be accomplished for example by digital software simulating a neural network.

In summary the multiband channelized receiver 36 splits the incoming analog signal into multiple channels each covering only a small fraction of the broad frequency band. The amplitude of the signal at the selected center frequency in each band serves as an input to the pattern recognition system. The pattern recognition system identifies the acoustical energy emission signature of a known reaction and provides a suitable output on a display screen not shown.

Figure 3:
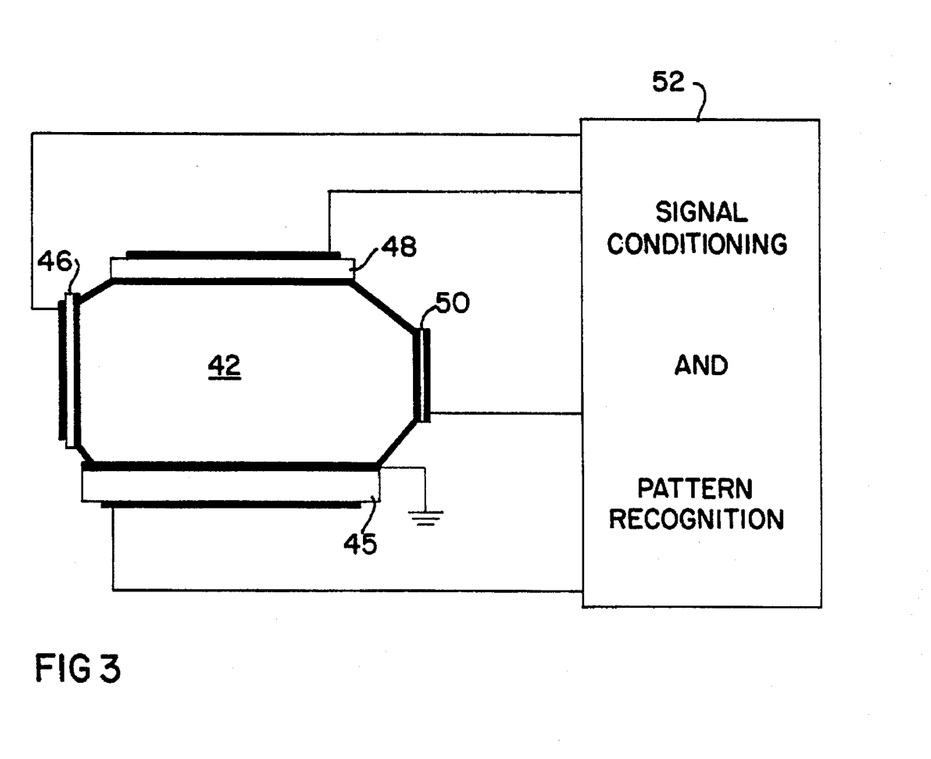
FIG. 3 is a simplified system block diagram of a measurement cell with a plurality of different independently mounted acoustic energy transducers and associated electronics for multichannel detection.

Another homogeneous bioassay for biorecognition events with channelizing of the acoustic emission signals is illustrated in FIG. 3. According to this example the reaction chamber 42 of a measurement cell 44 is bounded by four different acoustic sensors in the form of piezoelectric plates 45,46,48 and 50. The reaction chamber 42 contains for example the aqueous medium for determination of a binding reaction of biorecognition molecules. Typically one of the reactants such as a receptor molecule or DNA probe is known/unknown and the other reactant, the ligand or sample nucleic acid is unknown/known.

The reaction to be determined has previously been bioassayed for example in the system of FIG. 1 and the sensitive active or noisy frequencies associated with the binding reaction have been identified. The four piezoelectric plate acoustic sensors 45,46,48, and 50 have been selected to be responsive to a narrow band of acoustic frequencies each narrow band being centered on a frequency known to be characteristically active or noisy for the particular binding reaction. As heretofore described the acoustic sensor PZE plates are bounded by electrodes of a conductive metal which may be vacuum deposited, sputtered, or foil electrodes, typically gold. Each of the PZE plates is selected to have peak resonance at an odd multiple of the half wavelength of the center frequency ($n\lambda/2$ where n is odd) of an active or noisy band of acoustic energy emissions.

By placing multiple transducers that are sensitive and selective at different narrow frequency bands bounding the measurement cell, the channelizing function is now accomplished by the sensors themselves. Each individual transducer is designed for a different respective narrow frequency range or band, with peak resonance at an odd multiple of the half wavelength of the center frequency. Acoustic energy impedance matching layers are sandwiched between the respective PZE plates and measurement cell to pass the acoustic energy into the PZE plates with minimum reflection. The impedance matching layers can be selected to function as ¼ wavelength transformers. For that purpose, the thickness of Z matching layers is selected to be an odd multiple of the quarter wavelength ($n\lambda/4$ where n is odd) of the center frequencies of the narrow frequency bands of interest. The signals from the four respective plates are again appropriately amplified and conditioned for pattern recognition.

Figure 4:
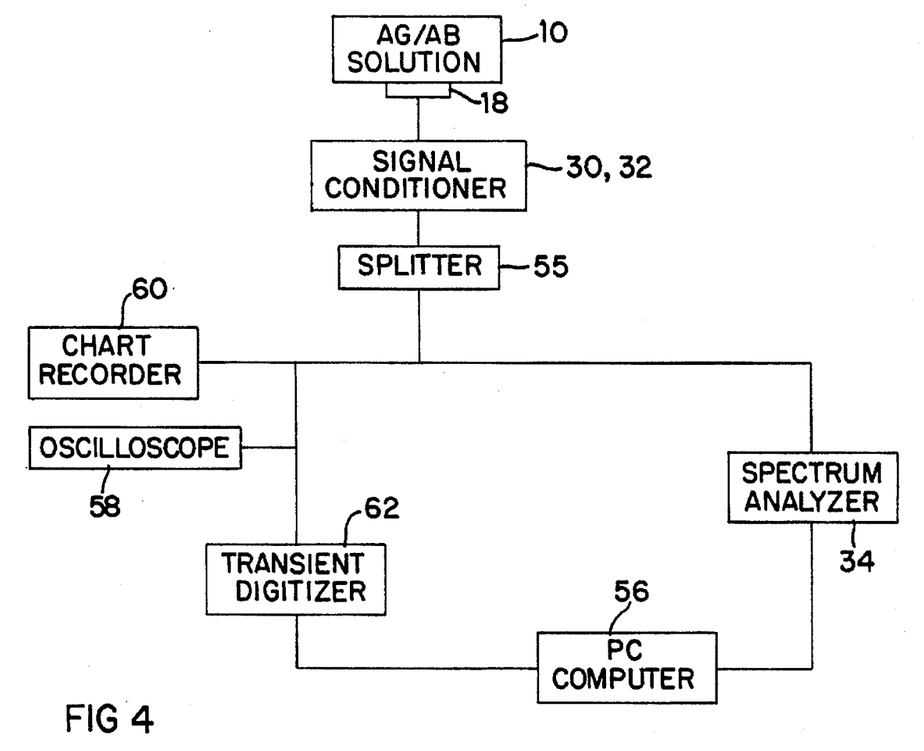
FIG. 4 is a simplified block diagram of a combined frequency domain and time domain acoustic emission sensor measurement system applicable for use in homogeneous bioassays.
Figure 5A:
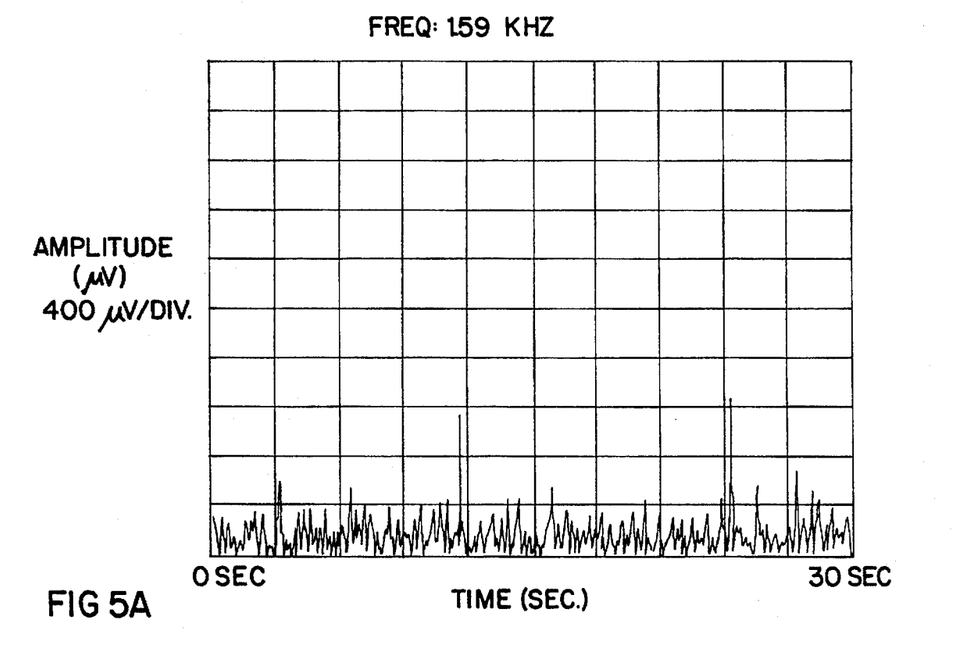
FIGS. 5A, 5B, 5C and 5D are graphs of acoustic energy emission frequency spectra at a frequency of approximately 159 KHz through four successive time intervals (amplitude spectra in the time domain) of a control binding reaction of affinity purified goat antibody to human IgG and mock antigen.
Figure 5B:
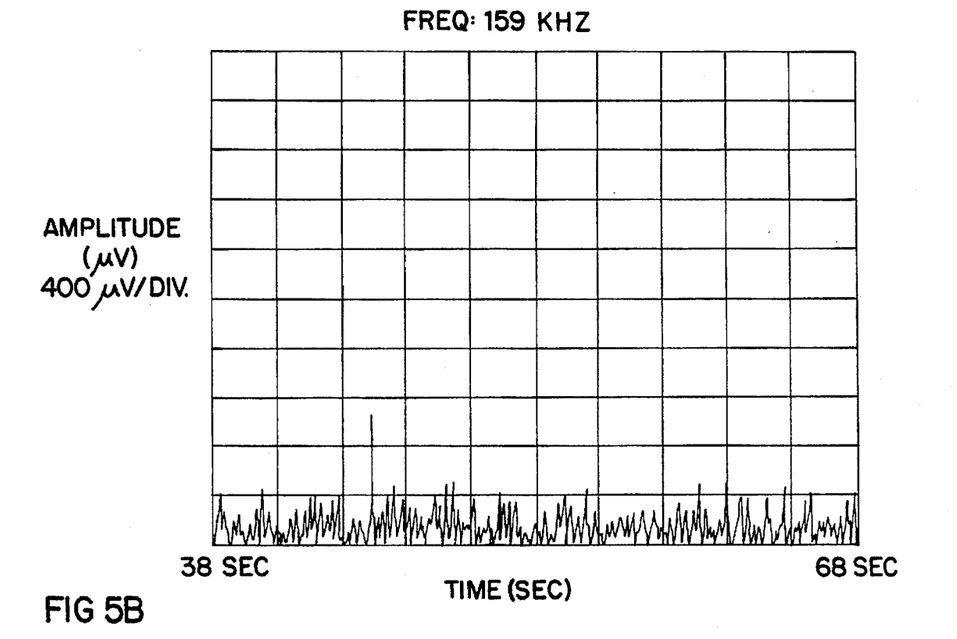
Figure 5C:
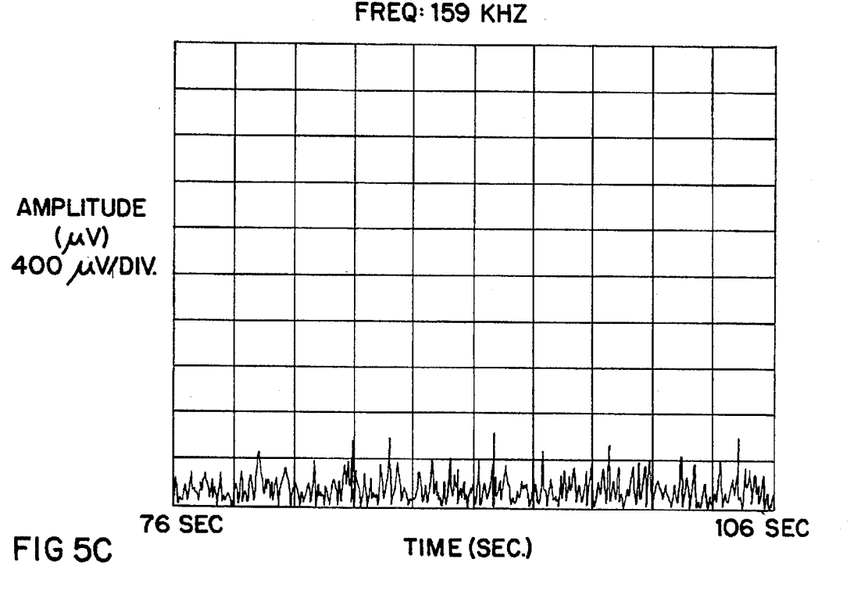
Figure 5D:
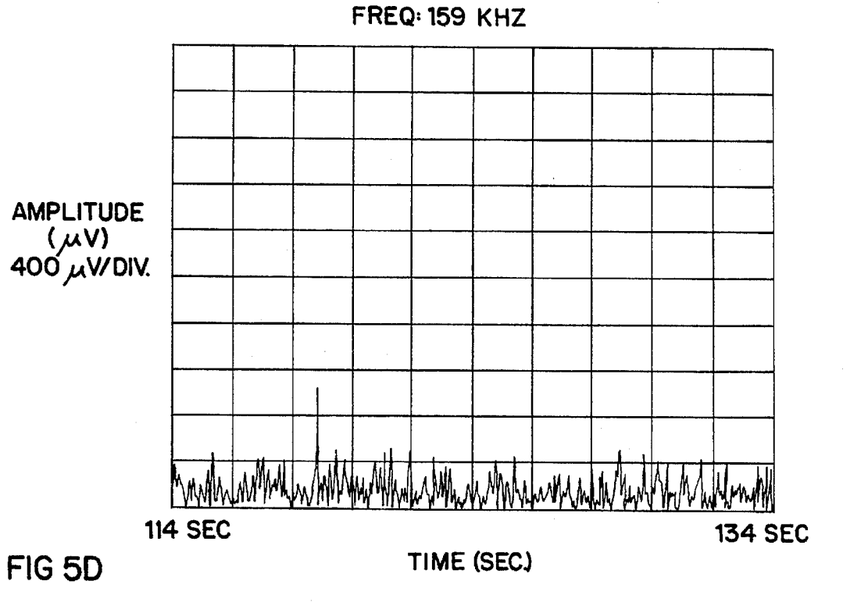

A generalized system for homogeneous bioassay of binding reactions of biological molecules is illustrated in FIG. 4. A measurement cell 10 contains a known/unknown antibody and unknown/known antigen solution for a binding reaction determination. The electrical analog signal from the acoustic sensor 18 is conditioned by amplifying and filtering to reduce environmental noise. The signal is then split by signal splitter 55 for simultaneous signal processing and analysis in the frequency domain and the time domain. For the frequency spectrum in the frequency domain one branch is coupled to spectrum analyzer 34 and a data acquisition system provided by microprocessor 56. The electrical analog signal corresponding to the acoustic emission signal of the particular binding reaction is converted into a frequency spectrum in the frequency domain using fast Fourier transform (FFT) software. A correlation procedure is used with reference to the frequency domain signal to extract the significant frequency responses.

In the other branch the electrical analog signal corresponding to the acoustic emission of the particular binding reaction is analyzed in the time domain. The other branch consists of an oscilloscope 58 and chart recorder 60. A transient digitizer circuit 62 includes a signal processing unit with a time domain correlator. The data acquisition system of the PC microprocessor then analyzes the data in the time domain. The electric analog signal corresponding to the acoustic emission is digitized and the correlation technique is used to differentiate the signal corresponding to the acoustic emission of the particular antigen/antibody reaction from the raw signal.

The center frequencies for the four narrow band PZE transducers may be selected to be for example 100 KHz, 300 KHz, 600 KHz, and 1 MHz. Other frequencies can of course also be selected through the GHz range and to the limits of ultrasonic technology. The center frequencies are of course selected to correspond with identified sensitive narrow band acoustic emissions of the particular binding reaction.

In the following example the change in solution properties of a homogeneous antigen/antibody binding reaction are directly and passively detected using acoustic emissions generated by the binding reaction. Both the antibody and antigen are prepared by dissolving in a solution. The immunological reaction of the antibody and antigen takes place in a measurement cell of the type illustrated in FIG. 1. The bivalent binding of antibody to multiple antigen sites results in rapid change in the local molecular properties which in turn generates a characteristic spectrum of acoustical waves. A frequency of 159 KHz was identified as an active frequency of the particular binding reaction hereafter described and the amplitude of the selected frequency was analyzed in the time domain using the system of FIG. 2 selecting only a single narrow frequency band centered on 159 KHz.

In the example of FIGS. 5 and 6 the antigen/antibody system selected for the binding reaction is human IgG antigen and goat antibody to human IgG. These immunoreagents can be obtained commercially and can be validated by repetition of the quality control steps described by the manufacturer. The affinity purified goat antibody to human IgG is examined for composition by immunoelectrophoresis (IEP) developed using anti-goat whole serum. It is compared with a purified goat IgG using a stained gel pattern with single gamma arc only. The activity and specificity of the goat antibody to human IgG is also validated in immunoelectrophoresis by using it as the development reagent following electrophoresis of a human serum sample. After the composition, activity and specificity is validated, quantitation is achieved based on an extinction value of 280 nm of 14 for a 1% solution of goat IgG in PBS. The human IgG antigen is similarly examined and validated for purity by immunoelectrophoresis and quantitation by absorbance at 280 nm.

As shown in FIGS. 5 and 6 a preliminary investigation of acoustic emission of the selected antigen/antibody system in the frequency domain resulted in selection of a narrow band center frequency of 159 KHz for investigation and analysis of amplitude distribution in the time domain at 159 KHz. This method allowed for continuous monitoring of the acoustic emission amplitude at 159 KHz in the time domain during four sequential 30 second intervals spaced 8 seconds apart.

Figure 6A:
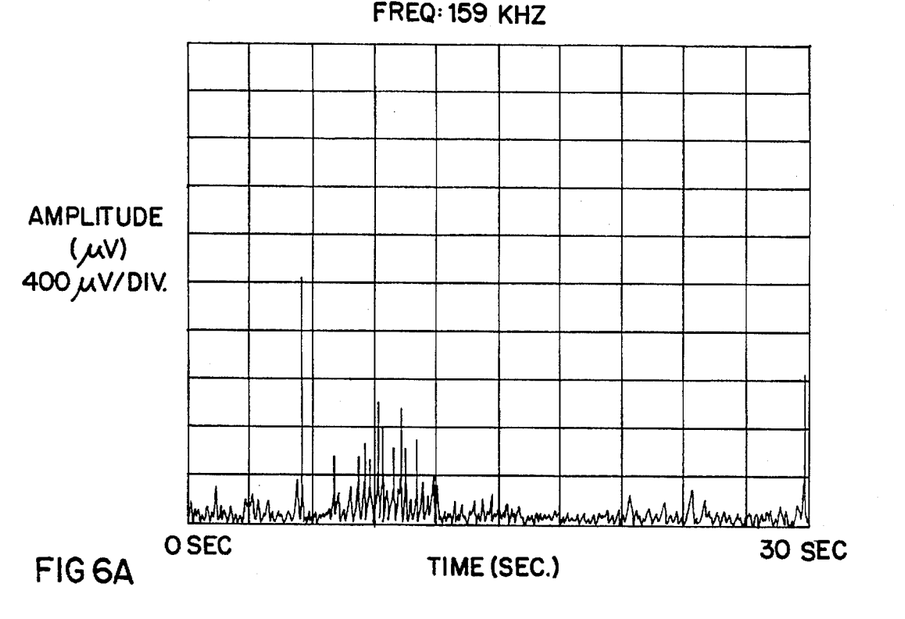
FIGS. 6A, 6B, 6C, and 6D are graphs of acoustic energy emission frequency spectra at approximately 159 KHz through four successive time intervals (amplitude spectra in the time domain) of a binding reaction of affinity purified goat antibody to human IgG and true human IgG antigen.
Figure 6B:
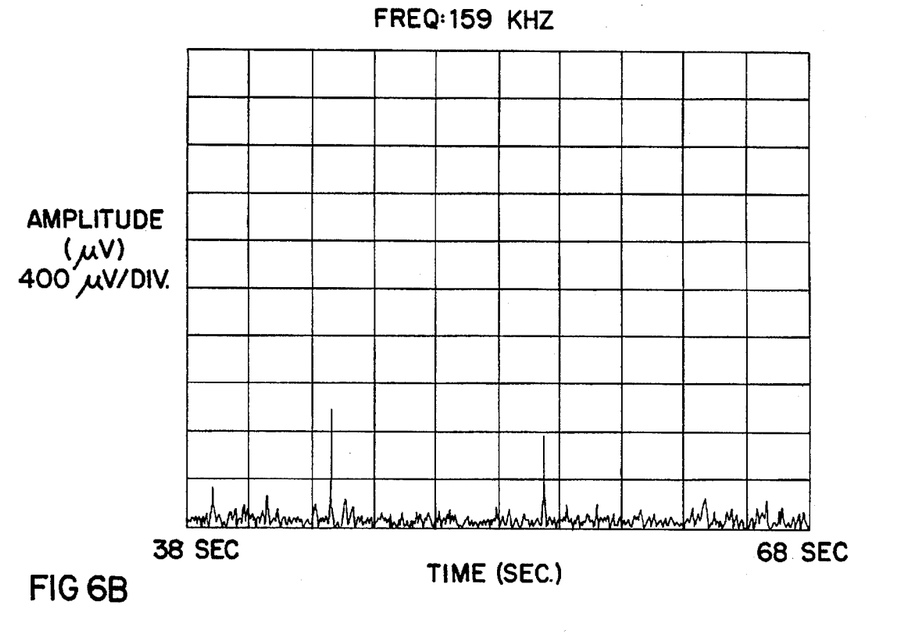
Figure 6C:
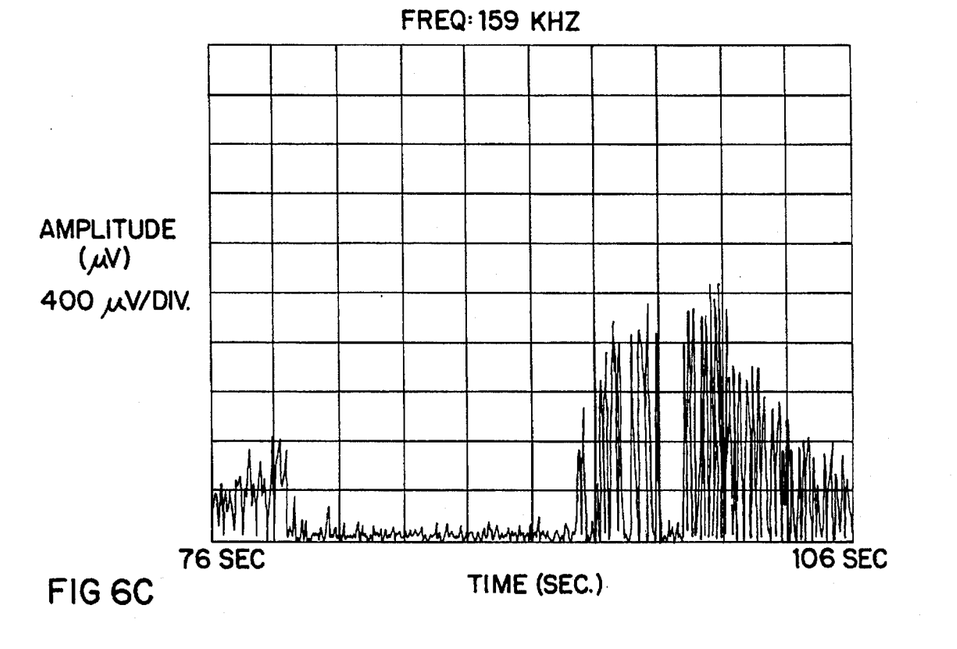
Figure 6D:
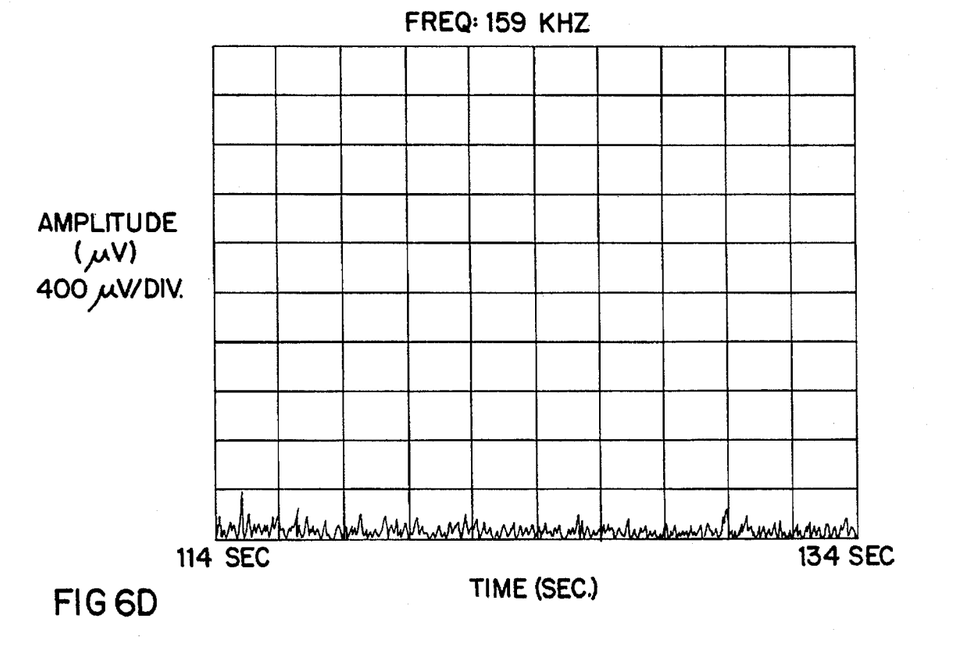

The data shown in FIGS. 5A-5D show the acoustic emission results using affinity purified goat antibody to human IgG with the addition of mock antigen to the solution in the reaction chamber of the measurement cell. As shown in FIGS. 5A–5D there was no acoustic emission response above background environmental noise. The data shown in FIGS. 6A–6D was generated using affinity purified goat antibody to human IgG mixed with true human IgG protein antigen in the reaction chamber of the measurement cell. There was a significant and strong acoustic emission response following the addition of human IgG antigen to the mixture. As shown in FIGS. 6A–6B the primary acoustic emission signals were generated between 7–12 seconds (see FIG. 6A) and again later at 76–80 and 94–106 seconds. The tail of the acoustic emission response at 106 seconds was cut off due to the 8 second delay before the next 30 second sampling interval.

Other frequencies may of course be selected for analysis in the time domain. For example investigation of a wider frequency range may identify a more active energetic frequency of acoustic emission for a particular immunological binding reaction for time domain analysis. Such investigation may span for example the KHz, MHz, and GHz frequency ranges and the limits of ultrasonic technology. With respect to immunochemical antigen/antibody binding reactions other applications of the invention include replacement of existing clinical assay methodology in the identification and quantitation of human serum proteins such as IgG, IgA, IgM, C3, C4, etc. The homogeneous bioassay can also extend the sensitivity limits of current methods so that analytes such as tumor markers, ferritin, and β2-microglobulin etc. can be measured rapidly. The system also permits immunospecific detection of macromolecules present in a turbid sample making possible and available food analysis in a homogeneous assay.

Figure 7:
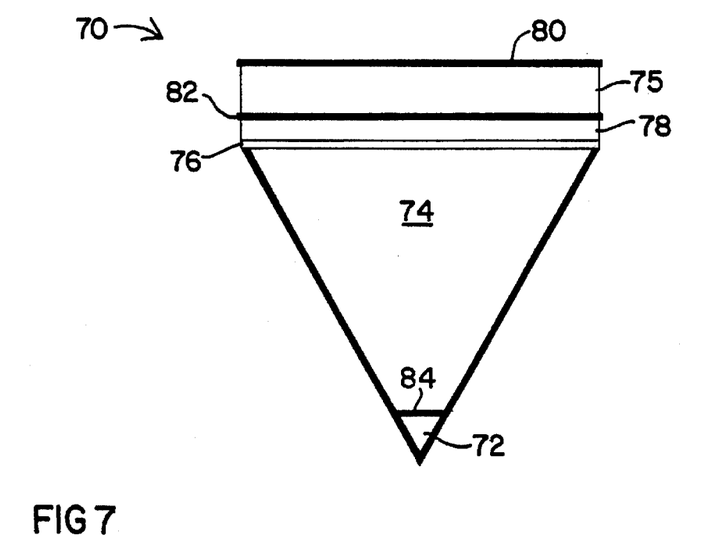
FIG. 7 is a simplified side diagrammatic view of a measurement cell for detecting acoustic energy emissions from a reaction chamber having a small size relative to the acoustic energy transducer and containing a binding reaction mixture of e.g. a ligand/receptor binding reaction or a complementary nucleic acid binding reaction.

An improved measurement cell 70 for use in the homogeneous bioassay is illustrated in FIG. 7. According to this example the reaction chamber 72 is limited to a small region at the point of a triangle or other polygon. By limiting the binding reaction of biorecognition molecules to a small reaction region, e.g. 0.1 ml to 1 ml, the source of acoustic emissions approximates a point source. The small acoustic emission source provides a substantially more coherent wave front particularly through the relatively large fluid propagation path 74. This arrangement also reduces interference effects in the acoustic energy emitted by the binding reaction.

In the measurement cell 70 of FIG. 7 the major portion of the area of the triangle is filled with an acoustic energy propagation liquid such as water and provides the fluid propagation path 74 leading to the acoustical detector in the form of a PZE plate 75. The expanding fluid propagation path permits use of a substantially larger detector or transducer for improving efficiency of collection of the acoustic energy. The reaction chamber 72 is restricted to the point of the triangle by an acoustically transparent partition 84.

As heretofore described impedance matching layers 76 and 78 can be interposed between the aqueous fluid propagation path 74 and the solid PZE disk 75. In the example of FIG. 7 a two stage impedance matching system is shown with two layers 76,78 having density and stiffness characteristics intermediate between the liquid in the fluid propagation path 74 and the solid PZE disk 75. PZE plate electrodes 80 and 82 are provided, electrode 82 typically grounded while the electrical analog signal corresponding to the acoustic emissions is derived from electrode 80.

The Z matching layers 76,78 can be constructed as quarter wavelength transformers. In that case the thickness of a particular impedance matching layer is selected to be an odd multiple of the ¼ wavelength (nλ/4 where n is odd) of the center frequence of a frequency band of interest in detecting a particular binding reaction.

Figure 8:
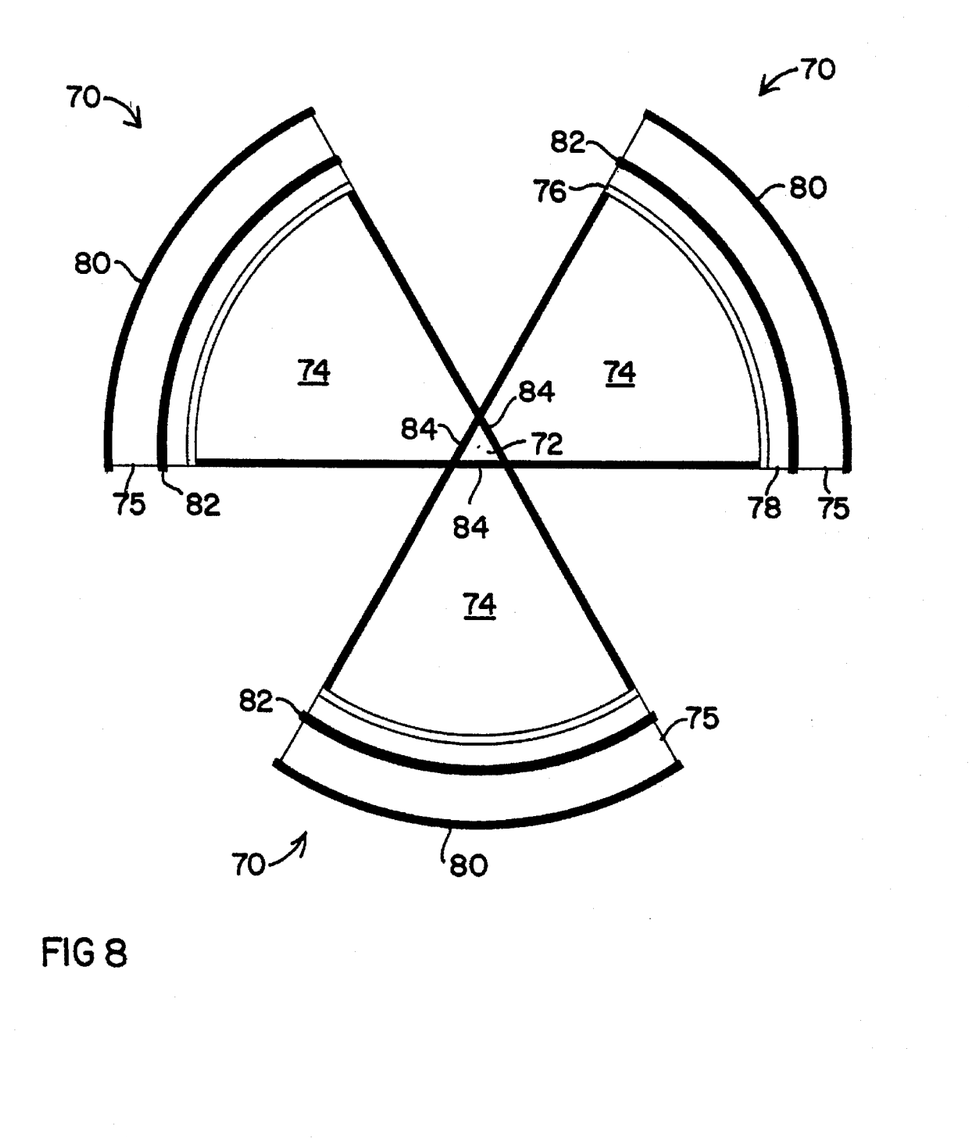
FIG. 8 is a simplified diagrammatic view of another measurement cell with a multisided binding reaction chamber and a plurality of passive acoustic energy transducers coupled to the sides of the reaction chamber.

As shown in FIG. 8 multiple measurement cells 70 can be arranged in a star arrangement around the reaction chamber 72 isolated from the respective fluid propagation paths by the acoustically transparent partitions 84. In this star configuration the acoustic sensor PZE plates 75 can be curved for improving electrical efficiency. Furthermore each of the acoustic sensor PZE plates 75 can be selected to be responsive to only a narrow band frequency range of acoustic emissions centered at different spaced apart frequencies. These center frequencies may be selected to be the active or noisy frequencies of a particular binding reaction for identifying the signature of the particular binding reaction by the amplitude distribution at the selected center frequencies in the time domain. Thus the multiband measurement cell of FIG. 8 provides another hardware arrangement for channelizing the acoustic emissions at the most productive or sensitive frequencies for identification and quantitation.

According to other embodiments of the invention a greater number of measurement cells 7 may be centered around different shape multisided polygons such as squares, pentagons, hexagons, etc. The number of triangular measurement cells 70 can be increased according to the number of sides of the polygon of the reaction chamber at the center of the star configuration. In this way the number of bands or channels can be increased according to the number of measurement cells 70 and different acoustic sensor PZE plates 75 tuned to the respective channels. Measurement cells can therefore be devised "tuned" to particular binding reactions of biorecognition molecules.

Yet another alternative embodiment for a multiband measurement cell is to use the single measurement cell of FIG. 7 and in place of the single acoustic sensor PZE plate 75 instead add a stack of PZE plate channel layers tuned to different narrow band frequencies with alternating layers of nonpiezoelectric glass, ceramic, polymer, etc. between the PZE plate layers and respective electrodes. The multilayer stack of PZE plates or layers alternating with non PZE layers and respective electrodes can be built up for example by successive vacuum deposition or sputtering. In this way a multiband transducer can be provided coupled to a single measurement cell for channelizing the acoustic emissions.

While the invention has been described with reference to particular example embodiments it is intended to cover all modifications and equivalents within the scope of the following claims.

We claim:

1. A system for homogeneous bioassay using acoustic energy comprising:

a measurement cell containing a binding reaction of mobile biorecognition molecules, said binding reaction selected from the group consisting of ligand/receptor binding reactions and complementary nucleic acid binding reactions, said complementary nucleic acid binding reactions selected from the group consisting of DNA/DNA, DNA/RNA, RNA/RAN binding reactions, PCR reactions and DNA/protein binding reactions;

a passive acoustic energy transducer coupled to the measurement cell for detecting acoustic energy emissions generated by a binding reaction of mobile biorecognition molecules and generating a corresponding analog electrical signal, said passive acoustic energy transducer comprising a wideband frequency response transducer responsive to a specified broad frequency spectrum of acoustic energy and constructed for peak resonance at an odd multiple ½ the wavelength of the center frequency of the specified broad frequency spectrum;

a signal conditioner for filtering and amplifying said electrical signal to provide a conditioned electrical signal;

and a signal analyzer for determining spectra of the conditioned electrical signal corresponding to characteristic acoustic energy emissions of the binding reaction of mobile biorecognition molecules.

2. The homogeneous bioassay system of claim 1 wherein the ligand/receptor binding reactions are selected from the group consisting of antigen/antibody binding reactions, enzyme/substrate binding reactions, lectin/carbohydrate binding reactions, and abzyme/substrate binding reactions.

3. The system of claim 1 comprising an elastic base abutting the transducer on the side of the transducer opposite the measurement cell to enhance bandwidth of the transducer.

4. The system of claim 1 wherein the signal analyzer is a frequency spectrum analyzer for determining frequency spectra in the frequency domain.

5. The system of claim 1 wherein the measurement cell comprises a reaction chamber having the passive acoustic energy transducer coupled to one side of the reaction chamber and an acoustic reflective lens on the opposite side of the reaction chamber for reflecting and focusing acoustic energy generated by a binding reaction of mobile biorecognition molecules onto the transducer.

6. The system of claim 5 wherein the acoustic reflective lens is a parabolic acoustic energy reflector.

7. The system of claim 1 wherein the measurement cell comprises a reaction chamber having the passive acoustic energy transducer coupled to one side of the reaction chamber and acoustic lens on the opposite side of the reaction chamber for reflecting and focusing acoustic energy generated by a binding reaction of mobile biorecognition molecules onto the transducer.

8. The system of claim 1 wherein the measurement cell comprises a flow through reaction chamber having an inlet end with multiple inlets for the reactants and an outlet end for flow through of a binding reaction mixture at a specified flow rate for continuous monitoring.

9. The system of claim 1 comprising a channelized multichannel receiver coupled to the signal conditioner for selecting at least one narrow frequency band.

10. The system of claim 9 wherein the signal analyzer is a time domain correlator determining amplitude spectra in the time domain.

11. The system of claim 1 wherein the passive acoustic energy transducer is coupled to the measurement cell by at least one impedance matching layer.

12. A system for homogeneous bioassay using acoustic energy comprising:

a measurement cell for containing a binding reaction of mobile biorecognition molecules, said binding reaction selected from the group consisting of ligand/receptor binding reactions and complementary nucleic acid binding reactions, said complementary nucleic acid binding reactions selected from the group consisting of DNA/DNA, DNA/RNA, RNA/RNA binding reactions, PCR reactions and DNA/protein binding reactions;

a passive acoustic energy transducer coupled to the measurement cell for detecting acoustic energy emissions generated by a binding reaction of mobile biorecognition molecules and generating a corresponding analog electrical signal, and wherein the acoustic energy transducer comprises a plurality of transducer plates responsive to different frequency bands or channels of acoustic energy for differentiating by channel the characteristic acoustic energy generated by the binding reaction;

a signal conditioner for filtering and amplifying said electrical signal to provide a conditioned electrical signal;

and a signal analyzer for determining spectra of the conditioned electrical signal corresponding to characteristic acoustic energy emissions of the binding reaction of mobile biorecognition molecules.

13. The system of claim 12 wherein the plurality of transducers plates are independently mounted on the measurement cell.

14. The system of claim 12 wherein the plurality of transducer plates comprises a stack of transducer plates mounted on the measurement cell.

15. The system of claim 12 wherein the plurality of transducer plates each comprise a narrow band frequency response transducer responsive to a different narrow frequency spectrum of acoustic energy.

16. The system of claim 15 wherein the signal analyzer is a time domain correlator determining amplitude spectra or amplitude waveform in the time domain.

17. The system of claim 16 wherein the signal conditioner is constructed to select a narrow frequency band of the electrical signal for amplitude spectra analysis in the time domain.

18. The system of claim 15 wherein each narrow band frequency response transducer is constructed for peak resonance at an odd multiple of ½ the wavelength of the center frequency of the specified narrow frequency spectrum.

19. The system of claim 12 wherein the measurement cell comprises a binding reaction chamber of multisided polygon cross section, and a plurality of passive acoustic energy transducer plates, each transducer plate facing a respective side of the reaction chamber, each transducer plate being acoustically coupled to the respective side of the reaction chamber by an acoustically transmissive medium, each transducer plate being responsive to a frequency band of acoustic energy generated by a distinct binding reaction of mobile biorecognition molecules.

20. The system of claim 19 wherein the plurality of transducer plates each comprise a narrow band frequency response transducer responsive to a different narrow frequency spectrum of acoustic energy, and wherein each narrow band frequency response transducer is constructed for peak resonance at an odd multiple of ½ the wavelength of the center frequency of the specified narrow frequency spectrum.

21. The system of claim 20 wherein the signal analyzer is a time domain correlator determining amplitude spectra in the time domain.

22. The system of claim 19 wherein the measurement cell comprises a three sided reaction chamber of triangular cross section and a plurality of three passive acoustic energy transducer plates.

23. The system of claim 19 wherein each passive acoustic energy transducer plate is curved to improve the sensitivity of the cell.

24. The system of claim 19 wherein said binding reaction chamber has a small volume relative to the volume of the acoustic energy transducer.

25. A method for homogeneous bioassay for an unknown analyte, said method comprising:

reacting in a measurement cell mobile biorecognition molecules in a binding reaction selected from the group consisting of ligand/receptor binding reactions and complementary nucleic acid binding reactions, said complementary nucleic acid binding reactions selected from the group consisting of DNA/DNA reactions, RNA/DNA reactions, RNA/RNA reactions, peptide nucleic acid/DNA reactions, PCR reactions and DNA/protein reactions, wherein said biorecognition molecules correspond to the unknown analyte;

detecting acoustic energy emissions generated by the binding reaction of mobile recognition molecules with a plurality of passive acoustic energy transducer plates responsive to different frequency bands or channels of acoustic energy for differentiating by channel the characteristic acoustic energy generated by the binding reaction and generating a corresponding analog electrical signal;

filtering and amplifying said electric signal; and analyzing spectra of the electrical signal corresponding to characteristic acoustic energy emissions of the binding reaction of mobile biorecognition molecules to identify the unknown analyte.

26. The method of claim 25 wherein the ligand/receptor binding reactions are selected from the group consisting of antigen/antibody reactions, enzyme/substrate reactions, lectin/carbohydrate reactions, and abzyme/substrate reactions.

27. The method of claim 25 comprising reacting in the measurement cell an antigen with an antibody one of which is known and the other unknown.

28. The method of claim 25 comprising detecting acoustic energy using a wideband frequency response passive acoustic energy transducer responsive to a specified broad frequency spectrum of acoustic energy.

29. The method of claim 28 comprising the step of analyzing the frequency spectra in the frequency domain.

30. The method of claim 25 wherein the plurality of transducer plates each comprise a narrow band frequency response transducer responsive to a narrow frequency spectrum of acoustic energy, and wherein each narrow band frequency response transducer is constructed for peak resonance at an odd multiple of ½ the wavelength of the center frequency of the specified narrow frequency spectrum.

31. The method of claim 30 comprising the step of analyzing amplitude spectra in the time domain.

32. The method of claim 25 wherein the measurement cell comprises a reaction chamber having the passive acoustic energy transducer coupled to one side of the reaction chamber and an acoustic reflective lens on the opposite side of the reaction chamber for reflecting and focusing acoustic energy generated by a binding reaction of mobile biorecognition molecules onto the transducer.

33. The method of claim 25 wherein the measurement cell comprises a binding reaction chamber of multisided polygon cross section, and a plurality of passive acoustic energy transducer plates each transducer plate facing a respective side of the reaction chamber, each transducer plate being acoustically coupled to the respective side of the reaction chamber by an acoustically transmissive medium, each transducer plate being responsive to a different frequency band of acoustic energy generated by a binding reaction of mobile biorecognition molecules.

34. The method of claim 33 wherein the measurement cell comprises a three sided reaction chamber of triangular cross section and a plurality of three passive acoustic energy transducer plates.

35. The method of claim 34 comprising filtering the electrical signal, selecting a single frequency band, and analyzing the signal amplitude in the time domain.

36. The method of claim 33 wherein measurement cell comprises a flow through reaction chamber having an inlet end with multiple inlets for the reactants and an outlet end for flow through of a binding reaction mixture at a specified flow rate and continuously monitoring the binding reaction.

37. The method of claim 33 wherein the acoustically transmissive medium comprises at least one impedance matching layer having a thickness of an odd multiple of ¼ the wavelength of the center frequency of the respective frequency band of the adjacent transducer plate.

38. The method of claim 25 comprising detecting acoustic energy using a narrow band frequency response transducer responsive to a narrow band frequency spectrum.

* * * * *